(12) United States Patent
Haldimann

(10) Patent No.: US 6,428,576 B1
(45) Date of Patent: Aug. 6, 2002

(54) SYSTEM FOR REPAIRING INTER-VERTEBRAL DISCS

(75) Inventor: David Haldimann, Zug (CH)

(73) Assignee: Endospine, Ltd., Cham (CH)

( * ) Notice: Subject to any disclaimer, the term of this patent is extended or adjusted under 35 U.S.C. 154(b) by 0 days.

(21) Appl. No.: 09/549,332

(22) Filed: Apr. 14, 2000

Related U.S. Application Data

(60) Provisional application No. 60/129,607, filed on Apr. 16, 1999.

(51) Int. Cl.$^7$ ................................................ A61F 2/44
(52) U.S. Cl. ................................................ 623/17.16
(58) Field of Search ...................................... 623/17.16

(56) References Cited

U.S. PATENT DOCUMENTS

| | | | | |
|---|---|---|---|---|
| 3,875,595 A | * | 4/1975 | Froning | 623/17.11 |
| 4,722,948 A | * | 2/1988 | Sanderson | 523/115 |
| 5,047,055 A | * | 9/1991 | Bao | 623/17.11 |
| 5,171,280 A | * | 12/1992 | Baumgartner | 623/17.11 |
| 5,324,775 A | * | 6/1994 | Rhee | 525/54.1 |
| 5,328,955 A | * | 7/1994 | Rhee | 525/54.1 |
| 5,556,429 A | | 9/1996 | Felt | |
| 5,571,189 A | * | 11/1996 | Kuslich | 623/17.11 |
| 5,583,114 A | * | 12/1996 | Barrows | 514/21 |
| 5,626,863 A | * | 5/1997 | Hubbell | 424/426 |
| 6,139,520 A | * | 10/2000 | McCrory | 604/60 |
| 6,183,518 B1 | * | 2/2001 | Ross | 623/17.16 |
| 6,235,043 B1 | * | 5/2001 | Reiley | 606/192 |

FOREIGN PATENT DOCUMENTS

| | | |
|---|---|---|
| WO | WO 97/26847 | 7/1997 |
| WO | WO 97/42986 | 11/1997 |

OTHER PUBLICATIONS

Dr. Hansen YUAN, Professor of Medicine at Syracuse University, Presentation at 13$^{th}$ Annual Meeting of North American Spine society, Oct. 30, 1998, San Francisco, California.

U.S. application No. 60/118,093, Hubbell et al., filed Feb. 1999.

Written Opinion from PCT examiner of International application No, PCT/EP00/03480, sections 3, 5 and 8.

* cited by examiner

Primary Examiner—Corrine McDermott
Assistant Examiner—Javier G. Blanco
(74) Attorney, Agent, or Firm—Lowe Hauptman Gilman & Berner, LLP

(57) ABSTRACT

A method of ameliorating the adverse effects of a defect in the annulus fibrosus by applying a curable bio-compatible material to the defect, and curing that material, in situ, into a cross linked visco-elastic solid polymer adhering to remaining annulus fibrosus and thereby closing said defect. Alternatively, the bio-compatible material may be cross linked immediately before insertion into the annulus fibrosus.

25 Claims, 3 Drawing Sheets

SYSTEM FOR REPAIRING INTER-VERTEBRAL DISCS

This application is a continuation in part of provisional application serial No. 60/129,607, filed Apr. 16, 1999, the entire contents of which are incorporated herein by reference.

INTRODUCTION

The present invention is directed to a system for repairing tissue defects in intervertebral discs. It more particularly is concerned with repairing the portion of an intervertebral disc that has been subject to damage, such as herniation, as well as to repairing that portion of an intervertebral disc remaining after the performance of a partial discectomy intervention. Such discectomies are conventionally performed to treat a severe hernia of an intervertebral disc.

REVIEW OF THE STATE OF THE ART

A disc hernia is a radial rupture of the annulus fibrosus of the intervertebral disc that is accompanied by a protrusion (sometimes a very large protrusion) of the annulus fibrosus and/or by an extrusion of disc material through the rupture in the annulus fibrosus. The rupture of the annulus fibrosus is often accompanied by a compression of the spinal canal and pressure on the nerve roots that pass through the disc protrusion or extrusion. This usually leads to strong and progressive pain that emanates from the compromised segment of the spine. This condition may require a surgical intervention.

Patients with a symptomatic disc hernia, and indication for a surgical intervention at the disc, normally undergo a partial or total discectomy operation. In a partial discectomy, protruding annulus disc material and a portion of the nucleus pulposus of the disc are removed. The resulting reduction in the volume of disc material within the epidural space leads to decreased pressure on the compressed nerve roots and/or the spinal cord, respectively. Without repair, the radial rupture defect in the annulus fibrosus will remain and will not close, at least it will not close in a relatively short time. Without repair, a considerable risk of post-discectomy complications, such as a re-herniation of the disc, will remain.

A successful discectomy intervention will result in lasting pain relief for the patient. However, it has been shown that severe post-discectomy complications may occur in about 6–16% of all surgical interventions. These are often caused by events such as a re-herniation of the disc, extensive epidural scar formation or vascularization and nerve ingrowth into the defect in the annulus fibrosus.

The cells of the nucleus pulposus produce cytokines and inflammatory mediators, such as nitric oxide, that have been shown to be responsible for nerve root irritation and sensitization that can lead to severe radicular pain. In a post-discectomy situation, without repair of the annulus fibrosus, nucleus pulposus material may migrate into the epidural space and/or nucleus pulposus-derived cytokines and inflammatory mediators may diffuse into the epidural space through the annulotomy site. Both events may result in post-discectomy complications such as persistent nerve root pain.

As a side effect of the volume reduction that is attendant upon a discectomy intervention, the intervertebral disc height, and thus the vertical distance between adjacent vertebral bodies, will be reduced. The decreased intervertebral disc height may be one of the reasons for a re-herniation of the disc. Further, the reduction in intervertebral disc height has been reported to lead to an accelerated mono-segmental degeneration of the annulus fibrosus or of the facet joints of the affected spinal segment.

Dr. Hansen YUAN (Professor of Medicine at Syracuse University) has recently presented a review of the available technology that is currently being exploited in connection with disc repair and replacement ($13^{th}$ annual meeting of the North American Spine Society, Oct. 30, 1998 in San Francisco, Calif. USA). According to an abstract of this presentation, many different people and groups are working on mechanical disc replacements, hydrogel implant replacements and in situ curable polyurethane disc replacements.

OBJECTS AND BRIEF DESCRIPTION OF THE INVENTION

It is an important object of this invention to provide means for reducing the incidence of post-discectomy complications by closing the annulus defect that remains after a discectomy surgical intervention.

It is another object of this invention to provide an in-situ curable sealant material that provides the surgeon with means for reducing the risk of re-herniation whilst leaving as much potentially regenerating nucleus pulposus tissue as possible within the disc space.

It is another object of the invention to provide means for closure of a ruptured or incised annulus fibrosus site after discectomy sufficient to seal the compartment restraining and surrounding the nucleus pulposus (portion) of the disc and to prevent later extrusion of further disc material (recurrent disc hernia).

It is another object of the invention to prevent, by sealing the annulus fibrosus, hypertrophic scar formation, vascularization, nerve ingrowth, or infection of the ruptured annulus fibrosus or in the nucleus pulposus cavity.

It is another object of the invention to prevent, by sealing the annulus, migration of nucleus pulposus cells into the epidural space, and to prevent, by sealing the annulus, diffusion of nucleus pulposus-derived cytokines and inflammatory mediators into the epidural space through the annulotomy site. The thus resulting prevention of contact between nucleus pulposus cells, and its cytokines or inflammatory mediators, with nerve roots after discectomy is another object of the invention and will assist to minimize nucleus pulposus-induced nerve root injury and nerve root pain.

It is another object of the invention to provide means to repair a ruptured annulus fibrosus, where the means functions as a sealant for the ruptured annulus fibrosus and, provided the nucleus pulposus contains a sufficient number of viable cells, assists in the restoration of the load-bearing and viscoelastic properties of the defective intervertebral disc.

It is another objective of the invention to provide an implant that minimizes removal of nucleus pulposus material during a discectomy intervention without having an elevated risk of recurrent disc hernia. Since the nucleus pulposus tissue in most disc hernia patients is viable and has regenerative potential, leaving as much nucleus pulposus tissue as possible in the disc space may be conducive to the gradually regeneration of the disc and restoration of its physiological functions.

Other and additional objects of this invention will become apparent from a consideration of this entire specification, drawings and claims.

In accord with and fulfilling these objects, one aspect of this invention comprises the use of compositions comprising an in-situ curable sealant(s), made of a bio-compatible material, to repair defects in an annulus fibrosus of an intervertebral disc. Such defects may be fissures and ruptures of the annulus fibrosus due to disc degeneration or disc hernia, as well as injuries due to incisions and punctures of the annulus fibrosus such as from annulotomy or discectomy procedures.

In general, defects in the annulus fibrosus have the shape of a complex radial cleft that extends from the innermost edge of the annulus fibrosus, that is at the border of the nucleus pulposus, to the outermost layers of the annulus fibrosus. The defect may originate A) because of a burst canal or rupture of the annulus fibrosus that permitted extrusion there through of material from the nucleus pulposus, or, B) by reason of incisions that had to be made during surgery in order e.g. to remove nucleus pulposus material from within the intervertebral disc that has caused a large bulge or protrusion of the disc.

Another type of defect of the annulus fibrosus is often observed in the case of severely degenerated intervertebral discs. In this condition, the disc tissue has become severely dehydrated and has lost its elasticity. As a result, the annulus fibrosus tissue has become brittle, friable and unstable to the extent that tissue fragments may come loose and migrate out of the annulus fibrosus, leaving space through which nucleus pulposus material can exude. These fragments are separated from the main body of the annulus fibrosus by numerous interconnecting fissures and are often held in place only by a thin outer lamella of the annulus fibrosus (see FIG. 3 for illustration). When this thin layer tears, the fragments may migrate into the epidural space and cause pressure on the spinal nerves, that in turn may cause severe pain.

Figure 1:
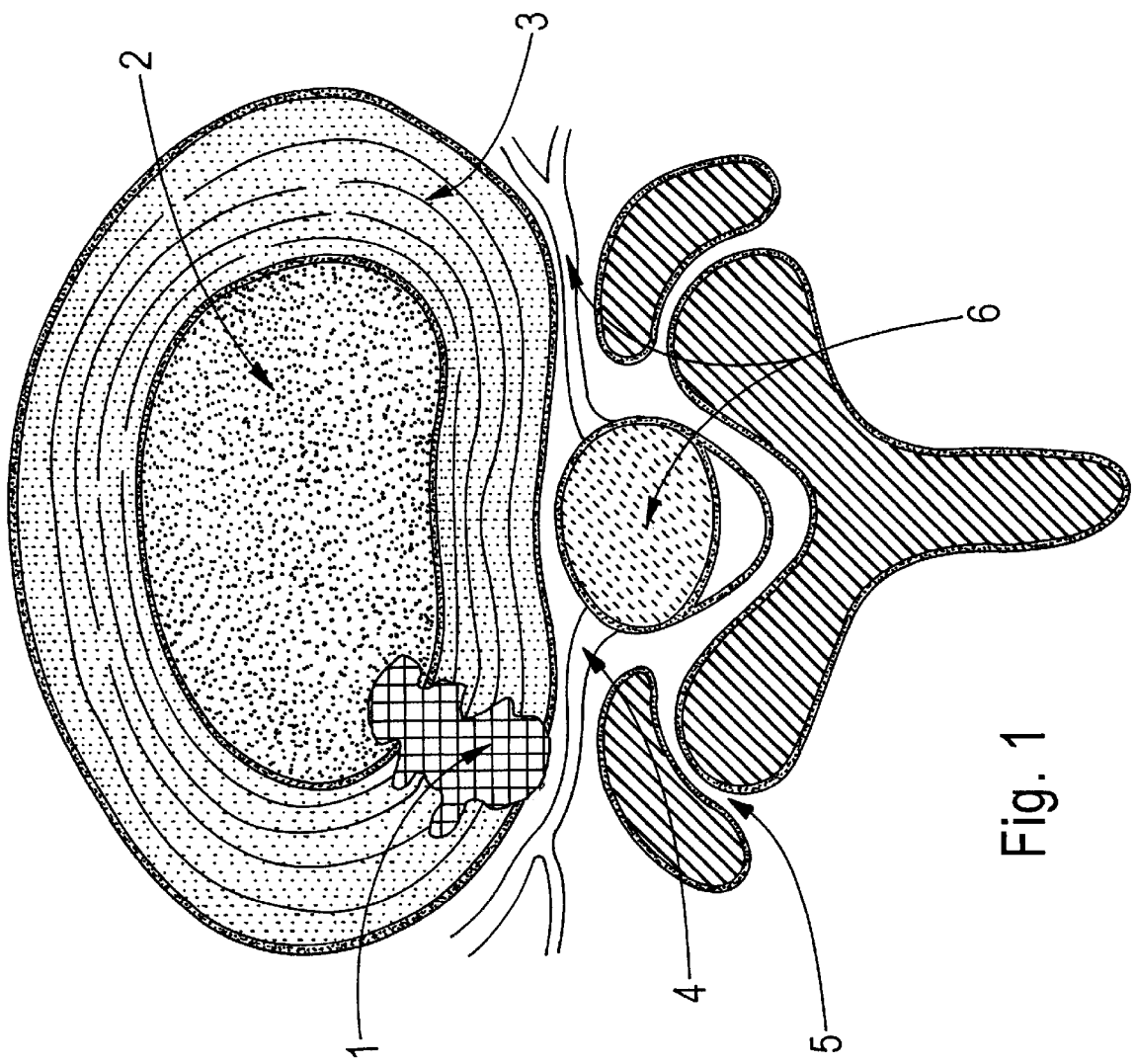
FIG. 1 is a cross-sectional view, in the horizontal plane of the lumbar vertebral column, showing a portion of a spinal column and including surrounding soft tissues. The intervertebral disc shown in the lower center has a large defect in its annulus fibrosus that has been closed with a sealant, according to this invention, for the annulus fibrosus.
Figure 2:
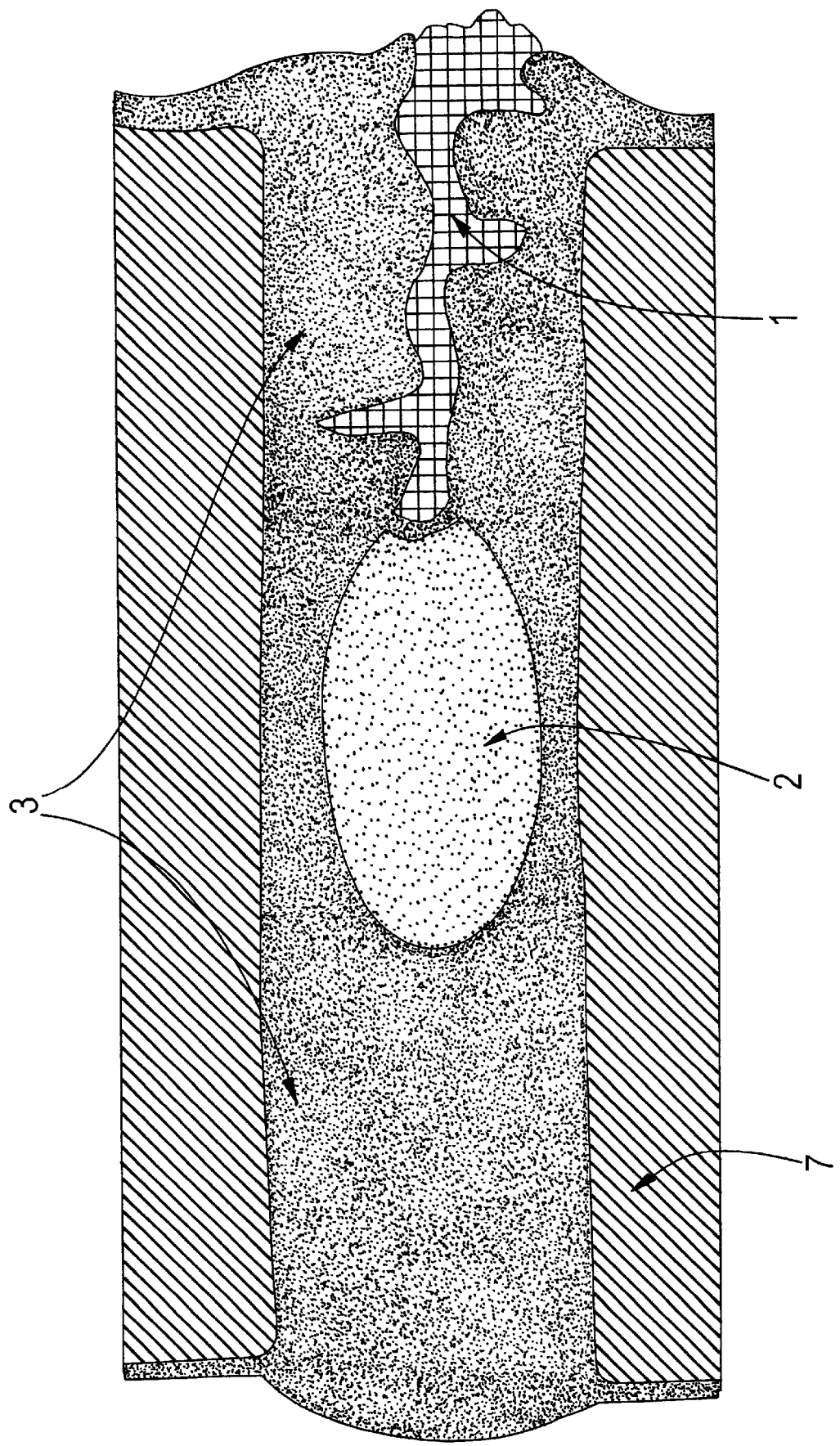
FIG. 2 is a cross-sectional view in the sagittal plane of an intervertebral disc. The annulus fibrosus is shown with a large defect that is filled with a sealant, according to this invention, for the annulus fibrosus.
Figure 3:
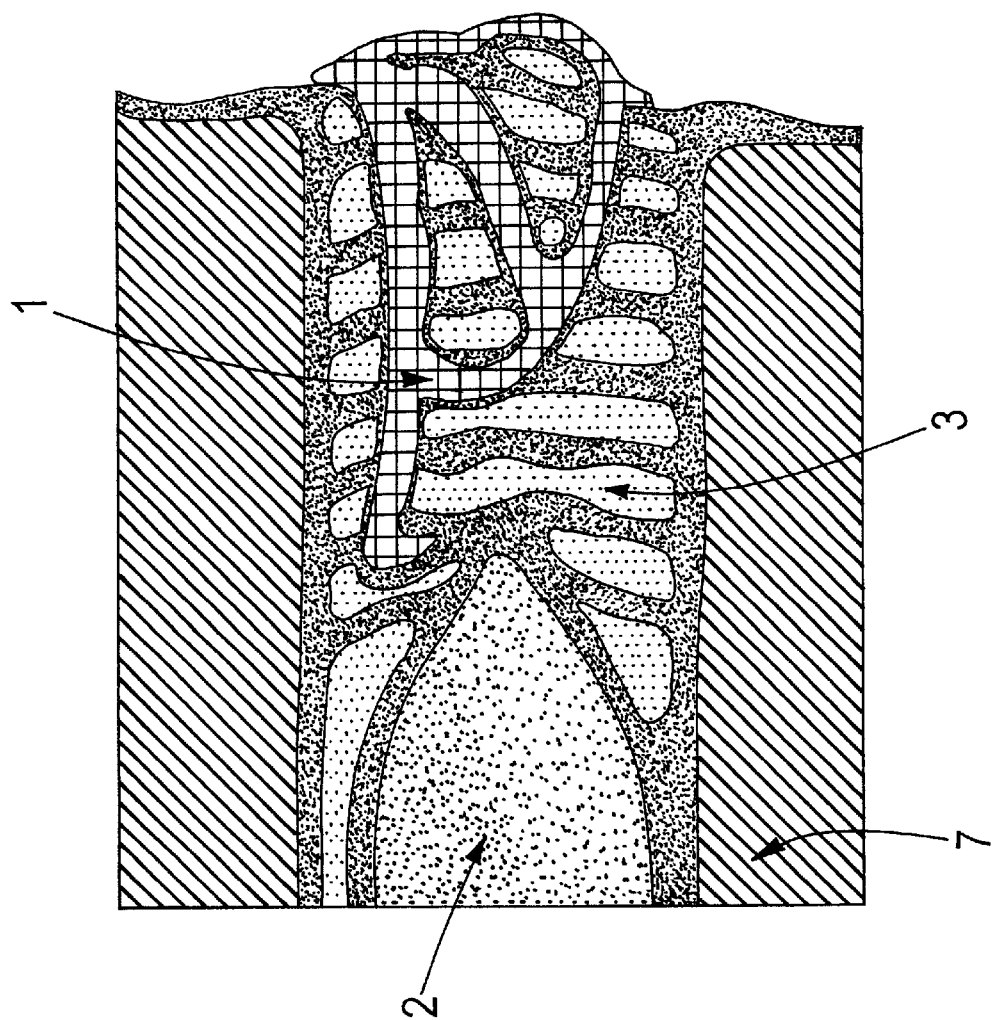
FIG. 3 is a cross-sectional view of a severely degenerated disc. On the right side, fragments from the outer annulus fibrosus are shown to be held in place by a thin lamella. Portions of the disc protrude to the right into the epidural space proximate to the spinal cord (not shown).

In the practice of the present invention, for repairing defects of the annulus fibrosus, the sealant composition of this invention may be applied in several ways, depending on the clinical situation with the disc degeneration. A particularly preferred application mode for the present invention is to put up the sealant composition as an injectable material. The composition is then injected into the proximity to the defect, whereupon it fills and closes incisions, clefts or fissures in the annulus fibrosus, such as occur after a disc hernia has been surgically treated. The sealant cures in-situ. In this particularly preferred application, the intervertebral disc is sealed in order to prevent a later extrusion of further disc material. This procedure is useful where the remaining nucleus pulposus is comprised of a sufficient amount of viable cells to perform its function. That is, this procedure is most useful where the amount of nucleus pulposus remaining in the disc after effecting repair is sufficient for the disc to continue to perform its intended function.

In another preferred application, the present invention can be used to patch up or consolidate brittle and friable tissue that exists in the outer annulus fibrosus of a severely degenerated intervertebral disc. In this application, the sealant composition of the present invention serves as a putty or cement in order to bind together the remaining tissue fragments of the outer annulus fibrosus. This procedure is preferably used as an alternative to the filling of a crevasse created by surgical intervention, as has been previously mentioned. However, it is also within the scope of the instant invention to both fill cracks or openings in the annulus fibrosus and cement together degenerated, but remaining, portions of the annulus fibrosus. This aspect of this invention does not particularly envision using the composition of this invention as a sealant for the entire disc, but such use can be accomplished. This application of the practice of this invention could also be described as annulus augmentation or partial annuloplasty, where the brittle annulus fibrosus is reinforced and stabilized through the in-situ curing of a sealant according to this invention. This application of the invention is intended to prevent tissue fragment migration and thus reduces the risk of spinal nerve compression by sequestrated fragments of the degenerated annulus fibrosus.

The bio-compatible compositions, comprising the in situ curable sealant of this invention, are based on materials that range in viscosity and physical state from an injectable liquid to a visco-elastic solid. The materials are preferably prepared from human or animal origin or may be made through conventional chemical synthesis or by a recombinant DNA technique. In general, it is important that the bio-compatible material compositions have the property of forming, upon curing, a strongly bonding, visco-elastic material that becomes sealed to the annulus fibrosus, or to fragments thereof, within about 2 to 40 minutes, preferably 2 to 10 minutes, after application (by injection or otherwise). The in-situ curing process must work well under wet conditions, at or near physiological pH (e.g. a pH of about 5–10), at or near physiological temperature (e.g. about 4–50° C.) and in the presence of interstitial body fluids (such as spinal fluid and/or blood). The sealant must cure to create a non-toxic, bio-compatible and strongly tissue adhesive seal of the annulus fibrosus or of materials that make up this feature. It should be of sufficient strength to stay in place without decomposition under permanent cyclic physiological loads.

A bio-compatible material that can serve as sealant of the annulus fibrosus has to meet exceptional characteristics with regard to its strength, tissue adhesion properties and bio-compatibility both when strategically placed and after curing. In addition, only an in-situ curing process of the biomaterial will form a sealant that perfectly conforms to the complex shape of a defect or incision in the annulus fibrosus.

Various bio-compatible material compositions have been described in the art. Some of these may be useful as in-situ curable sealants for defects of, or incisions in, the annulus fibrosus. None of the published disclosures of biomaterial compositions describe the potential application of such materials as in-situ curable sealants for use in connection with repair of the annulus fibrosus. Furthermore, none of the applications for the various bio-compatible materials that have been described in the prior art are similar or comparable to the use of such a sealant in connection with damaged annulus fibrosus. There are no disclosures in the prior art that described applications in which an uncured liquid bio-compatible material is caused to flow into a complex three-dimensional tissue defect, and therein to become cured whereby to seal or patch up the defect. There is no disclosure in the prior art that shows using such sealants bio-compatible materials to prevent re-herniation of the annulus fibrosus, or prevent, or at least minimize, annulus fibrosus tissue migration. Thus, this invention provides an annulus fibrosus sealing means, formed from in-situ curable formulations comprising flowable bio-compatible material, that can be caused to cure in situ.

DETAILED DESCRIPTION OF THE INVENTION

Preferred Bio-Materials

Preferred bio-compatible materials for use in the practice of the invention include all bio-compatible, hydrophilic synthetic or naturally occurring polymers that are curable to a visco-elastic end product under physiologic conditions. These polymers are cross-linked by an internal mechanism. That is, in some cases, no outside energy input or material is needed to cause the flowable bio-compatible polymers of this invention to become cured into a relatively permanently placed visco-elastic material. In other situations, the flowable bio-compatible polymers of this invention will need the input of outside influences, such as irradiation and/or heat, to cause them to cross link and become the desired visco-elastic materials. Such heat and/or irradiation can be very localized so as to cause the cross linking and curing to occur exactly where it is needed. In either case, the end product cross linked visco-elastic polymer materials will maintain its location, shape and structure, and lend stability and physical strength to a damaged annulus fibrosus. This can be on a permanent basis, that is the repairing sealant will become a permanent part of the annulus fibrosus.

It is also within the scope of this invention that the visco-elastic sealant used in this invention will be a temporary material that will bind and repair the damaged annulus fibrosus for a time sufficient to prevent re-injury of this member and to enable scar formation with fibrocartilaginous tissue to occur. This type of sealant will be composited such that it will degrade with time so that by the time the annulus fibrosus has accomplished sufficient self repair, the added sealant will have degraded and be expelled from the body. This cross-linking can be accomplished by making up a flowable mixture of two or more precursors molecules that react with each other over a short time to form the desired in situ cured visco elastic product that has physical and chemical properties that resemble those of the annulus fibrosus sufficiently to perform its function, at least substantially, while the natural annulus fibrosus regenerates itself. This flowable, in situ curable material may be made up of a single precursor that reacts with itself, e.g. by heating, or by irradiation with electromagnetic energy, such as visible or ultra violet light. It is also within the scope of this invention to use a one or plural component curable flowing material that is cured by the action of a catalyst and/or initiator that is included in the composition.

Some or all of the chemical compounds, cross linkable polymers, or pre-polymers, that form the precursor materials, or are the building blocks from which the precursor components are formed, can be bio-compatible, hydrophilic synthetic or naturally occurring polymers. Even if some of the precursor components are not especially bio-compatible, since they are intended for use within an animal, especially human, body, it is essential that none of these precursor materials themselves nor the polymers that result from their curing be detrimental to the animal, especially human, host. The cured polymer products are preferably completely bio-compatible, e.g. they do not induce extensive chronic inflammation, do not induce excessive complement activation, and do not induce excessive local cytotoxicity, such as for Example as a result of components that leach out of these cured or uncured materials. It is important that the cured polymers be hydrophilic, so as to form materials that are hydrogels, e.g. polymers with absorbed water contents in excess of approximately 25% of their own weight. The tissue specific compatibility of the resulting hydrogels is generally better than is the case with less hydrophilic materials. This is as a result of the water permeability of the hydrogel being similar to that of the surrounding tissue, and because of the better matching of the mechanical properties of the instant sealing material with the surrounding natural annulus fibrosus tissue.

The cured polymers that are useful in this invention may be synthetic or naturally occurring. It may be more reliable to ensure the long-term stability of a cured sealant that is based on synthetic polymers.

Alternatively, a controlled degradation can be engineered into a synthetic polymer by incorporation of slowly hydrolyzable linkages, such as for Example ester, amide, carbonate or anhydride linkages, into the cured polymer. Naturally occurring polymers generally will form sealing members that become more easily degraded in vivo, and there may be cases in which this is desirable, e.g. when the sealant is intended to be replaced by natural tissue that is being generated as a result of healing in the annulus fibrosus. This may be particularly desirable when the cured sealant member contains a bio-active agent to promote healing.

Examples of the type of synthetic polymers that can be used as building blocks in accord with this invention are polyethylene glycol, polyvinyl pyrrolidone, polyvinyl alcohol, polyacrylic acid, polyethoxazoline, polyhydroxyethyl acrylate, and polyhydroxyethyl methacrylate. These materials can be further functionalized in order to increase their ability to form hydrogels gels in situ.

Polysaccharides that are useful in the present invention include glycosaminoglycans such as hyaluronic acid, chondroitin sulfate A, chondroitin sulfate C, dermatan sulfate, keratan sulfate, chitin, chitosan, heparin, and derivatives or mixtures thereof. Further, proteoglycans such as decorin, biglycan and fibromodulin may also be used in the present invention. Proteoglycans are components of the extracellular matrix of cartilage cells and contain one or more glycosaminoglycan molecules bound to a core protein. Furthermore, mixtures of various species of glycosaminoglycans or proteoglycans with various proteins, or mixtures of various species of glycosaminoglycans or proteoglycans with proteins can be used in the practice of the present invention.

Various synthetic polypeptides can also be used in the practice of the present invention. The term "synthetic polypeptide" is intended to encompass polypeptides that have been produced using recombinant DNA techniques, as well as those produced by other methods of chemical synthesis.

Various naturally occurring proteins such as albumin, collagen, fibrin and elastin may also be used alone or in combination with other materials in the practice of the present invention.

The terms "albumin" "collagen" or "elastin" or "fibrin" as used herein refer to any types of these naturally occurring proteins, from any source, including, but not limited to, protein extracted from tissue or fractionated from blood or recombinant proteins. Further, these terms refer to all forms of these naturally occurring proteins, including those that have been processed, denatured or otherwise modified.

In general, collagen, elastin, fibrinogen or fibrin from any source may be used in the practice of the present invention. The preparation of purified, non-immunogenic proteins from human or animal tissues as well as recovered by different methods of producing recombinant human collagen or fibrin are thoroughly described in the literature.

Collagen of any type, including, but not limited to, types II, III, V. VI, IX or any combination thereof, are preferred to be used in the practice of the present invention, although collagens of type I and type II are generally the most preferred types. Collagen for use in the present invention may be in a fibrillar or non-fibrillar form. The preferred form of the preferred collagen for the practice of the present invention is the fibrillar form of collagen due to its higher persistence and mechanical strength.

Elastin of any type can be used for the practice of the present invention. Elastin of type I is generally preferred.

Preferred Bio-Material Compositions for the Sealant of This Invention

In a preferred embodiment of the present invention, the sealant for the damaged annulus fibrosus is a bio-compatible polymer composition of viscosity that is sufficiently low to permit injection and which forms a visco-elastic material upon becoming cured. The bio-compatible polymer precursor(s), when implanted in the situs of the defect in the annulus fibrosus, are flowable material(s), preferably a liquid of suitable viscosity such that when the liquid conforms to the damaged area of the annulus fibrosus, it tends to stay in place while it is curing in situ.

In general, the preferred material composition for use in the practice of the invention is an in-situ curing, bio-compatible polymer composition that has, when cured, the properties of an elastic, or visco elastic, substantially solid hydrogel. The preferred bio-compatible polymer material composition may include two or more precursor components that are dissolved or dispersed in two different solvents/carriers, A) and B). The solutions/suspensions are suitably mixed immediately prior to the application of the sealant into the situs of the damage. Alternatively, a single solution containing the appropriate bio-compatible material composition can be used in combination with a separate initiator system to start the curing reaction, as for Example the composition disclosed for a different purpose in U.S. Pat. No. 5,626,863.

A preferred bio-compatible material composition that is useful for sealing damage to the annulus fibrosus is made of two precursor components, a bio-compatible material solution and an activated crosslinking agent. In this preferred composition, bio-compatible materials, such as collagen or glycosaminoglycans, and cross linking agents, such as synthetic hydrophilic polymers as disclosed for a different purpose in U.S. Pat. Nos. 5,324,775 or 5,328,955, can be used. Preferred synthetic hydrophilic polymers for use in the invention include bifunctionally activated polyethylene glycols, as disclosed for a different purpose in U.S. Pat. Nos. 5,326,955 or 5,583,114.

Another preferred bio-compatible material composition for the sealant of a damaged annulus fibrosus is made of two precursor components, a buffered protein solution and a bifunctional cross linking agent. More specifically, the protein is preferably be a non-immunogenic, water soluble protein. Materials such as serum albumin or derivatives of elastin, fibrinogen or collagen can be used as protein, and polyethylene glycol, with activated terminal groups may be used as the preferred cross linking agent in this preferred composition. Such a composition is disclosed for other purposes in U.S. Pat. No. 5,583,114.

Another preferred bio-compatible material composition that is useful for the sealant of the annulus fibrosus according to this invention is made of a polymerizable component that includes a water soluble core region and polymerizable terminal group(s) or functional group(s). In addition, the component may include a biodegradable extension of the core region. A preferred embodiment of this aspect of this invention includes polyethylene glycol as the core region and one or more acrylate moieties as the polymerizable end cap or terminal portion, as disclosed for other purposes in U.S. Pat. No. 5,626,863. In the practice of using this component as in-situ curable sealant for the damaged annulus fibrosus, a free radical polymerization reaction of the component must be initiated, either after the composition has been placed at the situs, or immediately prior to introduction of the composition into the damaged area(s) of the annulus fibrosus. For initiation of the polymerization immediately prior to application, the polymerizable component may be extruded from a syringe or a piston-driven cartridge and passed through a light or temperature conducting cannula before it reaches the situs of the annulus fibrosus defect. The free radical polymerization reaction may be initiated through photo-initiation by UV or visible light irradiation of the cannula. In the case of a thermal polymerization initiator system, as disclosed in U.S. Pat. No. 5,826,803, the cannula may be heated to a controlled temperature that is not higher than about 48° C. For initiation of the free radical polymerization reaction in situ, either a thermal polymerization initiator system, that is sensitive to a temperature of about 37° C. or, alternatively, chemical initiation systems may be used in the practice of the present, invention. Such systems are disclosed for other purposes in U.S. Pat No. 5,626,863.

A particularly preferred bio-compatible material composition that is useful for sealing damage in an annulus fibrosus is made of two precursor components that can co-polymerize in a self-selective manner, such as by a nucleophilic addition reaction, as disclosed in pending U.S. patent application Ser. No. 60/118,093, filed on or about Feb. 1, 1999 in the names of Jeffrey A. Hubbell, Donald L. Elbert, and Alyssa Panitch, and carrying an attorney's docket number ETH 103. The entire contents of this provisional patent application, which was copending with the parent provisional application of the instant application, is incorporated herein by reference. In a preferred embodiment, a hydrophilic linear or crosslinked polymer with two or more terminal unsaturated groups is used as the first precursor component, and another hydrophilic polymer with two or more terminal nucleophilic groups is used as the second precursor component. In a particularly preferred embodiment, polyethylene glycol constitutes the hydrophilic polymer, acryloyl moieties are used as unsaturated end groups, and compounds with thiol functional groups are used as the nucleophilic groups. Such compositions are disclosed in this provisional patent application.

When using this embodiment in the practice of the present invention, the two precursor components should be quickly mixed immediately prior to use and then applied to the annulus fibrosus defect using a common applicator. As a preferred embodiment, the two components may be filled into a dual syringe or a dual-chamber piston-driven cartridge. Both chambers of the syringe, or the cartridge, have openings that merge together into one outlet tube. This tube, is fitted with a suitable mixing nozzle, such as a spiral mixer nozzle, that serves as a static mixer for the two components when they are pressed out of the syringe and passed through the nozzle. As the mixed components are pressed out of the tip of the nozzle, they can be directly applied into the operation situs, i.e. the damage or defect site of the annulus fibrosus.

It is desirable for the mixed bio-compatible material composition to have a low surface tension in relation to physiological materials such as fluids and the annulus fibrosus, and a good intrudability into such systems. These properties permit the bio-compatible material to optimally penetrate into micro-fissures that may be present at the application site of the annulus fibrosus. The intrusion of the biomaterial into micro-fissures and clefts of the damaged annulus fibrosus allows for a strong mechanical interlocking with the natural tissue at the application site and helps to mechanically secure the sealant within the application site during the curing time.

The term "intrudability" relates to the ability of a liquid material composition to penetrate into complex microstructures and to fill small voids. This intrusion or penetration into said microstructure may be caused by low injection pressures, gravitation, capillary forces or non-covalent interactions between the liquid and the microstructure. The intrudability of the mixed biomaterial composition can be increased by including one or more bio-compatible fluid lubricants or surfactants, for Example dextrose, maltose, glycogen, dextran, dextran sulphate, hyaluronic acid glycerol, phospholipids polyoxyethylene sorbitan esters or polyethylene/polypropylene glycols.

Various particulate materials may also be incorporated into the bio-compatible material compositions for use in the invention. Suitable particulate materials include, without limitation; particulate elastin fibers and crosslinked or non-crosslinked fibrillar collagen.

Various biologically or pharmaceutically active agents may also be incorporated into the bio-compatible material compositions for use in the invention. Examples of active agents include, without limitation, growth factors, differentiation factors, enzymes, receptor agonists or antagonists, antibodies, hormones, analgesics, local anesthetics, anti-inflammatory drugs, such as Indomethacin and tiaprofenic acid, antibiotics or anti-microbial agents. The term "active agent" as used herein refers to molecules, usually organic, that exert biological effects in vivo. This term also encompasses combinations or mixtures of two or more active agents.

Summary of Discloses Medical Applications of Bio-Compatible Material Compositions that are Suitable as Sealant for the Annulus Fibrosus The patents listed above describe various methods of using in-situ curable bio-compatible material compositions in the field of soft and hard tissue surgery, such as to position tissue flaps, to attach side grafts, to prevent air leaks in pulmonary surgery, to inhibit bleeding, to avoid unwanted tissue adhesions, to fill and augment any void spaces in the body, or more generally to close undesired lesions and fissures such as fistular orifices or cysts.

However, these prior art patents do not describe or mention an application or method of using such materials as an in-situ curing sealant to treat defects in the annulus fibrosus and thereby to create an annulus sealing device. There is also no prior art that describes applications that are similar or comparable to the specifications and objectives of a sealant for the annulus fibrosus, as described in the following two sections. Specifically, none of the prior art describes applications in which a liquid or semi-solid biomaterial is caused to flow into a complex three dimensional annulus fibrosus tissue defect, to seal or patch up the defect and prevent a re-herniation or annulus tissue migration, and assists to restore, at least partially, the hydrodynamic function of the intervertebral disc.

Thus, there is described an annulus sealing device, comprising in-situ curable biomaterial formulations that cure to a visco elastic member that at least partially simulates the structure, physical properties and biomechanical functions of the annulus fibrosus and maintains the integrity of this member permanently or for a time sufficient to enable the regeneration of the natural annulus fibrosus tissue.

Description of Important Features of the Sealant for the Annulus Fibrosus According to This Invention Because of the unique bio-mechanical and physiological properties of the intervertebral disc in general and the annulus fibrosus in particular, a functioning and efficient sealant for the annulus fibrosus should meet numerous specifications, even if it replaces just a small portion of the damaged natural tissue of the annulus fibrosus.

The sealant of the annulus fibrosus is implanted in a low-viscosity liquid form, thus allowing the implanting material to penetrate into tears and micro-fissures with a width of at least 100 micrometers that are interconnected with a radial rupture or principal defect of the annulus fibrosus.

The sealant of this invention for the annulus fibrosus has the property of becoming strongly attached to the surrounding tissue of the annulus fibrosus by close interlocking and entanglement of its shape with the structure of the annulus fibrosus surrounding the defect and by filling cavities in the nucleus that were created during discectomy, thus forming an inner portion of the implant that has a larger cross section than the protrusion canal. The adhesion of the sealant to the surrounding annulus fibrosus tissue is enhanced through polar group interaction or chain inter penetration between the hydrophilic implant material and the surrounding tissue. In addition, covalent bonds formed between the preferred hydrogel bio-compatible material and the surrounding annulus fibrosus tissue further increase and secure the attachment of the sealant of this invention to the annulus fibrosus tissue in proximity to the defect in the annulus fibrosus.

The annulus sealing material that seals the defects in the annulus fibrosus may be the result of the interaction of at least two bio-material precursor components that react with each other in situ, preferably in a self selective reaction. Alternatively, a single bio-compatible material precursor composition that is activated for polymerization, such as for Example by activation either in situ or application immediately prior to implanting, may be used. Both systems result in a sealant that substantially perfectly conforms to the complex and irregular shape of an annulus fibrosus defect and bonds strongly to the tissue surrounding the defect. In addition, the self-selectivity of the reaction is an important feature to minimize toxic or denaturing effects of the curing bio-compatible material composition.

The sealant of the annulus fibrosus is preferably formed from previously pre-polymerized materials that are employed as prepolymer or macromer precursor components. In this way, the risk of exposing a patient to volatile and toxic residual monomers that may remain after curing of the sealant can be avoided.

The sealant of the annulus fibrosus must have adequate impact and tensile strength and must be adequately resistant to fatigue from repetitive loading and unloading or repetitive torsion moments that the annulus fibrosus is conventionally subjected to. This allows the sealant to permanently stay in place and remain intact after implantation. An even more important property of the sealant of the annulus fibrosus is its ability to withstand intradiscal pressures of the nucleus pulposus in the upper physiological range and to efficiently seal the annulus fibrosus so that the nucleus pulposus is contained within the intervertebral disc.

The sealant of the annulus fibrosus closes the defect in the annulus fibrosus so as to reduce the risk of a recurrent disc hernia and to prevent the further extrusion of nucleus pulposus material through the defect, thus avoiding contact between nucleus pulposus cells and its cytokines or mediators with nerve roots after discectomy and preventing or minimizing nucleus pulposus-induced nerve root injury and nerve root pain.

The sealant of the annulus fibrosus assists in the restoration of the physiological function of the herniated intervertebral disc. In particular, the sealant of the annulus fibrosus assists the nucleus pulposus to restore its hydrodynamic function after a discectomy intervention by being able to gradually build up the physiological intradiscal pressure. This will also allow the intervertebral disc to act as a cushion for physiological cyclic loads and to gradually restore the normal disc height and thus protect the facet joints in the damaged segment from excessive and long term loads.

The sealant of the annulus fibrosus has adequate viscoelastic properties due to its water content and strong three dimensional network of interconnecting polymer molecules. This minimizes the creep behavior of the sealant and enables it to withstand cyclic loads under physiological conditions for long periods without significant degradation and without losing elasticity.

The material composition for the sealant of the annulus fibrosus may be radio-opaque to a similar degree as a polymethyl-methacrylate based bone cement that is commonly used for the fixation of joint replacement prostheses. This feature is intended to allow the surgeon to monitor the correct implantation of the implanted sealant per-operatively and to identify the implant post-operatively in an X-ray radiograph.

The preferred final water content of the cured implant is about 30% to 90%. Generally, the final implant water content increases as the concentration of PEG (polyethylene glycol) in the precursor component solutions decreases.

According to this invention, the sealant of the annulus fibrosus is highly bio-compatible and is well tolerated in the body due to its following properties: A) it is preferably a hydrogel material that is hydrophilic and water-permeable similar to the surrounding tissues, B) the sealant material is non-toxic and C) the sealant material has a stiffness coefficient, in relation to the application of physiological loads and stresses, such as in compression, tension, and axial rotation, that is the same as or less than the stiffness coefficient of the natural annulus fibrosus tissue.

By being as strong as, but softer than, the surrounding tissue, friction, if any, between implant and surrounding tissue remains low and stress-shielding of the tissue is avoided. By avoiding friction with the implant and stress-shielding of the surrounding tissue, the conditions for a normal long term remodeling of the annulus tissue are optimized and the risk of gradual implant rejection or hypertrophic tissue reactions is minimized. The sealant for the annulus fibrosus is permeable to water and water soluble substances, such as nutrients, metabolites, drugs and the like.

The sealant for the damaged annulus fibrosus may also serve as a carrier and controlled release drug delivery system for topical applications of drugs for anti-inflammatory, antibiotic, analgesic or other therapies. In the case of a non-biodegradable sealant for the annulus fibrosus, the release mechanism is primarily based on diffusion of the drug through the cross linked sealant and into contact with other elements of the body where therapy is required. In the case of a hydrolytically stable, bioerodible material composition for the sealant, the drug release rate will be steady and predictable and will be proportional to the controlled bioerosion of the sealant material over an extended period of time, while newly formed annulus fibers and nucleus tissue gradually replace the sealant material put in place according to this invention.

Preferably, the sealant for the annulus fibrosus may also function as a carrier for the controlled release of various growth and/or differentiation factors, such as basic fibroblast growth factor (bFGF), insulin-like growth factor (IGF), transforming growth factor beta (TGF), platelet derived growth factor (PDGF), chondromodulin (ChM), bone morphogenic protein (BMP), etc. For the successful administration of these auto- or paracrine growth factors, a biologically relevant concentration must be maintained in the disc tissue over an extended period of time. Due to its proximity to the annular lesion, the sealant for the annulus fibrosus, when used as a carrier for the controlled release of growth factors, may allow for an excellent bioavailability of the mentioned growth factors covering a therapeutic window of several weeks or months.

General Mode of Use and Administration of the Sealant

In the preferred form of the invention, the precursor components are stored in a piston driven, one or two chamber cartridge that serves as a transport and storage container. Each chamber of the cartridge is closed by a sealing membrane within the extrusion flange at the tip of the cartridge.

In preparation for using the sealant, the sealant application system comprising the application instrument, precursor filled cartridge, mixer nozzle (for two component systems) and injection cannula has to be prepared. To do so, the precursor filled cartridge is placed into an application instrument that serves to press the pistons of the cartridge in a reproducible and volume controlled manner. Immediately prior to the injection of the sealant, the sealing membrane of the cartridge is broken and a spiral or other mixer nozzle (for two component systems) is attached onto the extrusion flange. An injection cannula with a blunt ended tip is placed on top of the mixer nozzle that allows for precise application of the sealant into even narrow defects of the annulus. If necessary, electromagnetic radiation, such as UV or visible light, or heat is supplied through a light or temperature transparent/conducting cannula before the sealant reaches the application site.

The sealant for the damaged annulus fibrosus; can be applied post operatively at the end of a standard micro-discectomy surgery with the patient in prone position. For application of the sealant, the cannula of the prepared application system is placed deep into the defect or incision of the annulus fibrosus in such a way that the tip of the cannula is proximate to the inside edge (that is the edge of the annulus fibrosus that boarders on the nucleus pulposus) of the cavity created by removal of disc tissue during discectomy. This placement is followed by injecting the precursor components of the sealant of this invention into the defect until the defect is completely filled, which typically requires ½ to up to about 2 ml of precursor component volume. As the precursor components are pressed out of the cartridge, they are mixed in the nozzle and, dependent on the bio-compatible material composition used, the polymerisation or nucleophilic addition reaction, that results in the curing of bio-compatible material composition, is initiated. Because of its low viscosity and low surface tension as compared with physiological fluids, the mixed precursor components are able to penetrate into micro-fissures in the degenerated or remaining (after the discectomy) annulus fibrosus tissue that are interconnected with the radial cleft.

In the preferred form of the invention, the two precursor components of the sealant cure in situ within more than about 2 minutes but less than about 10 minutes to form a solid visco-elastic polymer hydrogel implant that conforms to the shape of the annulus fibrosus defect. The thus formed implant becomes closely interlocked with the annulus fibrosus structure that surrounds the defect and is inherently shaped to conform, when cured, to the shape of the defect in the annulus fibrosus that it has filled.

EXAMPLES

The following Examples are provided to describe and illustrate the practice of the invention and not to limit or to restrict the scope of the invention. It will be apparent to those skilled in the art that certain changes and modifications may be practiced within the scope of the present invention.

The following protocols, materials and procedures may be partly modifications of procedures and adaptations of materials reported in U.S. Pat. Nos. 5,324,776, 5,328,956, 5,626,863, 5,324,775; 5,328,966; 5,583,114; 5,626,863 and the above referred to co-pending provisional patent application. All of these references are incorporated herein by reference, respectively.

Example 1

A 105 mg/ml (10.5% W/V) aqueous solution of fibrillar collagen in 0.05 M sodium bicarbonate buffer and 0.15 M sodium chloride is adjusted to pH 9.5. 2.5 ml of this biomaterial solution (solution A) is aspirated into a dual chamber polypropylene cartridge through one of the two extrusion flanges of the cartridge. 2.5 ml of a solution of difunctionally activated N-succinimidyl carbonate PEG (DSC-PEG, MW 3600) in 0.005 M sodium carbonate/bicarbonate buffer and 0.15 M sodium chloride at pH 6.0 and in a 1 to 10 molar ratio of collagen (solution A) to DSG-PEG (solution B) is filled into the second chamber of the cartridge.

Both chambers of the cartridge are closed by attaching a spiral mixer nozzle (3.2 mm inner diameter, 6.2 cm length, 0.38 ml void volume) onto the dual extrusion flanges. The cartridge is placed into a manual application instrument that allows for a reproducible and volume controlled extrusion of the bio-material in increments of 0.5 ml per step. A blunt tip aspiration needle (18 gauge, 90 mm length) is placed on the tip of the mixer nozzle. Immediately prior to this application of the sealant, the handle of the application instrument is pressed three times (3×0.5 ml) in order to fill the void of the mixer and needle with the mixed bio-material precursor solutions. About 1 ml of mixed precursor solution flows out of the needle tip and is discarded. The cross linking process is now activated and care must be taken to apply the sealant without delay, i.e. within less than about 60 seconds in this Example.

A bovine cadaveric lumbar trunc is placed in prone position (spine axis horizontally with spinal processes facing up) and prepared with a standard posterolateral microdiscectomy approach using a 4 cm outer incision. The annulus fibrosus is incised posterolaterally with a full thickness square incision (fenestration with size: 3 mm×3 mm). The loose annulus tissue is then removed from the fenestration site with a 2 mm rongeur, followed by removal of at least one gram or one ml of nucleus pulposus tissue—in order to create the typical operation situs at the end of a lumbar discectomy. All of this is done prior to activating the crosslinking process. The needle tip of the sealant applicator is placed about 2 cm deep into the disc, near the bottom of the nucleus cavity that has been created by the incision. About 1–2 ml of sealant is extruded by pressing the handle of the application instrument (preferably at a rate of about 2 steps per second), until the sealant fluid appears at the outside edge of the incision and forms a convex bulge on the outer periphery of the disc. The needle is then withdrawn from the incision and the sealant allowed to cure for 5 minutes.

Example 2

A 380 mg/ml (38% w/v) aqueous solution of human serum albumin (MW 68000) in 0.1 M sodium bicarbonate buffer and 0.15 M sodium chloride is adjusted to pH 8.2 (solution A buffered protein solution). A 200 mg/ml (25% w/v) aqueous solution of difunctionally activated N-succinimidyl propionate PEG (DSP-PEG, MW 3400) in 0.01 M sodium carbonate/bicarbonate buffer at pH 6.0 is prepared as solution B (cross linking agent). Solutions A and B are placed in the dual chamber cartridge and applied in the animal annulotomy model as described in Example 1. In this Example 2, the application of the sealant without delays is particularly important because of the short curing time of this type of sealant (2–3 minutes).

Example 3

180 mg/ml (18% w/v) of PEG tetraacrylate (MW 8200) is dissolved in a buffer of 0.02 M sodium phosphate at pH 7.4 and 0.15 M sodium chloride. Ammonium persulfate (0.01 M) and sodium bisulfite (0.005 M) are added to the solution that now represents the polymerizable bio-material with thermal polymerization initiation system. 5 ml of this bio-material solution is aspirated into a polypropylene syringe that is fitted with a Luer type adapter tip. The syringe is closed by placing a temperature-controlled, flow through heating cylinder, that is connected to a control unit, onto the tip of the syringe. The syringe is placed into a manual application instrument that allows for a reproducible and volume-controlled extrusion of the bio-material in increments of 0.25 ml per step. A blunt tip aspiration needle (18 gauge, 90 mm) is placed on the tip of the heating cylinder. The handle of the application instrument is pressed four times (4×0.25 ml) in order to fill the void of the heating cylinder and needle with the bio-material solution. About 0.2 ml of bio-material solution flows out of the needle tip and is discarded.

Immediately prior to the application of the sealant, the heater is turned on and the heater control unit is set at 50° C. As soon as the heater reaches a temperature of 45° C., the polymerization process will start and care must be taken to apply the sealant without delay, i.e. within less than about 15 seconds and at a rate of approximately two steps per minute (0.5 ml of volume/min).

The sealant is applied in the animal annulotomy model as described in Example 1.

Example 4

Equal volumes of 10 mM phosphate buffered saline (PBS), adjusted to pH 9.0 with triethanolamine ((EtOH)$_3$N), and of 10 mM PBS, adjusted to pH 9.0 with iN NaOH, were combined to form a PBS pH 9.0 solution. In 1 ml of this solution, 893 mg of pentaerythritol tetrakis (3-mercaptopropionate)(QT) were dissolved. This solution represents solution A (solution of polymer with terminal nucleophilic groups). Solution B was made up of 2.1 g of polyethylene glycol diacrylate having a molecular weight of 570 (PEGDA 570). Both solutions were combined and mixed well by vortexing. Air bubbles were removed by sonicating. The mixture was cast in polypropylene molds to form cylindrical testing samples of biomaterial, and allowed to cure for 60 minutes at room temperature. The resulting cured biomaterial has a solid material content of 75% (w/w) or 72% (v/v), respectively. This biomaterial, when tested in displacement controlled compressive stress mode, demonstrated an ultimate strength of more than 2 MPa and withstood deformations of about 35% in compression.

Example 5

Solutions A and B were prepared as described in Example 4. After mixing solutions A and B by vortexing, 100 microliters of the mixture was placed between 20 mm plates of a CVO 120 rheometer with a gap of 100 um. The mixture was maintained at 37° C. while the elastic modulus, complex modulus and viscosity were followed with time using shear at 1 Hz with a strain amplitude of 0.3. With progression of the reaction. the two combined precursors showed a gel point, defined by the time when the elastic modulus becomes greater than the complex modulus. Using these testing conditions, the gel point occurred in about 11 minutes.

Example 6

Mechanical properties of cross-linked hydrogel systems can be manipulated by using bi- or multimodal molecular weight distributions in the material compositions. Including a low molar content of a high molecular weight precursor in a low molecular weight system can synergistically combine properties from either molecular weight component and improve the mechanical properties of the material as compared to gels formed from either molecular weight component alone. For Example, a system composed of cross-linked low molecular weight materials may be strong, but may not elastically withstand large deformations (strain) in compression or tension. Systems composed of cross-linked high molecular weight materials with long polymer chains may withstand tremendous strains, but at the cost of decreased strength. A preferred bimodal hydrogel system combines predominately short polymer chains with a small molar ratio of the longer chains and results in biomechanically relevant stress and strain resistance properties.

Solution A was prepared as described in Example 4. 1.37 g of polyethylene glycol diacrylate with a molecular weight of 570 (PEGDA 570) and 440 ul of 1-methyl-2-pyrrolidone were mixed and heated to 50° C., while 0.73 g of polyethylene glycol diacrylate with a molecular weight of approx. 20,000 was slowly added and allowed to dissolve. This solution represents solution B.

Solutions A and B were mixed and tested as described in Example 4. The resulting hydrogels showed an ultimate strength of more than 3 MPa and withstood deformations of about 60% in compression.

Example 7

Including inorganic particles as components of cross-linked hydrogels is a way to render the sealant of the annulus fibrosus radio-opaque. Furthermore, addition of sub-micrometer sized particles to hydrogels can be used as a way to modulate the mechanical properties of the cured biomaterial gels.

Solution A was prepared as described in Example 4. Solution B was made of 2.1 g of polyethylene glycol diacrylate with a molecular weight of 570 (PEGDA 570) that was loaded with 300 mg of BaSO4 particles type blanc fixe (10% w/w), with an average particle size of 800 nm. Solutions A and B were combined as described in Example 4. The cured biomaterials resulting from addition of the BaSO4 were highly radioopaque and showed a stiffness of 55 N/mm, representing a 30% increase in stiffness over the biomaterials described in Example 4. Further, a similar material composition was prepared that contained 10% of fumed silica particles with an average particle size of 14 nm instead of the above $BaSO_4$ particles. The cured material resulting from this precursor composition showed significant increases in its ultimate strength. After 100 cycles, with 4 MPa of maximum load in compression stress testing, these materials had not failed.

Example 8

Including lubricants or surfactants into the material composition for the sealant of the annulus fibrosus can be used both to increase the tissue intrudability of the uncured sealant material and to improve the mechanical properties of the cured sealant material.

Solution A was prepared as described in Example 4. Solution B was made of 2.1 g of polyethylene glycol diacrylate with a molecular weight of 570 (PEGDA 570) that was mixed with 30 mg of sorbitan monooleate. Solutions A and B were combined as described in the previous Example 5, resulting in a biomaterial with a final concentration of 1% (w/w) of sorbitan monooleate. The resulting gels exhibited a similar increase in ultimate strength compared to the gels with inorganic particles added, as described in Example 8, but without the associated increase in stiffness.

Example 9

Toxicity and biocompatibility of the low molecular weight components of the material composition for the sealant of the annulus fibrosus according to this invention can be improved by pre-reacting these components, such as to obtain higher molecular weight components with remaining functional groups.

1.89 g of PEG hexathiol that was obtained through a reaction of tetrakis (3-mercaptopropionate) pentaerythritol (QT) and PEG diacrylate (MW=575), was suspended in 0.48 ml of PBS buffer at pH 9.0 by sonication. The mixture represents solution A. Solution B was 2.1 g PEG tetraacrylate that was obtained through in a reaction of a 10-fold excess of PEG diacrylate (MW=575) with QT. Both solutions were combined, mixed and biomaterial gels were prepared as described in Example 4. The resulting biomaterial gels demonstrated mechanical properties similar to those already described in Example 4; i.e. better than 2 MPa for ultimate strength and a stiffness of 40 N/mm.

Example 10

Sterile solutions A and B from Example 4 were combined with sterile sorbitan monooleate and $BaSO_4$ particles and the quantities described in Examples 7 and 8. Gel pins of 1 mm in diameter and 10 mm length were prepared using the same procedure as described above in Example 4, except that the mixture of solutions A and B was placed in molds to form pins prior to gel formation.

The pins were implanted into the right or left lumbar posterior muscles of rabbits. Pins made of polyethylene were implanted on the controlateral side of the animal as reference implants. After 4 weeks, the animals were sacrificed and histological sections of the implants and the surrounding tissue were performed. With both gel types tested, no significant differences were apparent compared to the reference materials. Rare macrophages, fibroblasts and neovessels were associated with the implanted gel pins. No necrosis, degeneration or any other local intolerance signs were induced by these material compositions.

The same gel compositions were also injected into the lumbar intervertebral discs of rabbits in situ. A small injury in the lumbar intervertebral disc of the rabbit was created with a needle. A sham injury was also created two segments cranial from the segment of the first defect.

Not earlier than 5 minutes before implantation, the sterile solutions A and B were each filled into 1 ml syringe cartridges and mixed by simultaneously passing the contents of both cartridges through a spiral mixer nozzle element, as described in Example 1. Because of the small volumes of sealant needed in this animal model, the mixture was transferred into a 1 ml syringe and injected into the defect with a 22G needle.

After 4 weeks, the animals were sacrificed and the implant and sham sites sectioned for the preparation of histological slides. Histological work-up showed that the injected materials gelled in situ, were in close contact with. the surrounding tissue and had no specific reaction associated with the tissue. No activated immunologic cells were detected and no necrotic or degenerative processes were seen and only rare active macrophages and giant cells were observed.

Example 11

Lumbar spines from 2 to 5 year old Merino sheep are freshly dissected from levels L1 to L7. All muscles and all posterior bony and ligamenteous structures, and also the anterior longitudinal ligament, are removed. These spines are then cut into single-joint segments by transversal sections through the vertebral bodies in order to obtain functional anterior spinal units with intact intervertebral discs for testing. Subsequently, the functional anterior spinal units are frozen at −20° C. and 5 holes of 3 mm diameter and 10 mm length are drilled into the annulus from the anterior portion of the annulus and in radial direction.

Before testing, the functional anterior spinal units with annulus holes were thawed and the upper and the lower half of the vertebral bodies are embedded in polymethylmethacrylate. A gel composition is prepared, freshly mixed and applied to the disc as described in Example 10, i.e. the mixed composition is injected into one of the previously drilled holes in the annulus. Immediately thereafter, a screw with 1.5 mm diameter is placed 7 mm deep into the middle of the gel position that has been filled into the hole and held in place for 15 minutes to allow for the curing of the gel composition.

The anterior spinal units, with sealant and screw implanted into the annulus fibrosus, are then placed in a universal testing machine (Zwick TN 05) fixed in a vice with a 200 N pre-load and with the screw axis in the vertical direction and with the screw head facing up. A vertical pullout force is applied to the screw head at a constant controlled rate of 0.1 N/min, until pullout of the implant from the annulus, which is defined as a strain rate in excess of 10 mm/min in these testing conditions. The maximum force obtained before pullout is used to calculate the bio-adhesion or ultimate shear stress on the interface between the implant material and annulus fibrosus tissue. The implanted gel composition in this example can be subjected to a shear stress of more than 10 kPa without failure.

In the accompanying drawings, the following reference numbers indicate the identified elements for the drawing:

1 Sealant in annulus defect
2 Nucleus pulposus
3 Annulus fibrosus
4 Epidural space
5 Facet joint
6 Spinal cord and nerve root
7 Bone of vertebral body The following references are pertinent to the instant invention:

ORAL PRESENTATION:
YUAN, Hansen, Paper Presented at 13$^{th}$ Annual Meeting of the North American Spine Society, Oct. 30, 1998
U.S. Patent Documents
U.S. Pat. No. 5,324,776 June 1994 Rhee et al. Class 525/54.2(Collagen Corp.)
U.S. Pat. No. 5,328,956 June 1994 Rhee et al. Class 525/54.1(Collagen Corp.)
U.S. Pat. No. 5,583,114 July 1994 Barrows et al. Class 514/21 (3 M Corp.)
U.S. Pat. No. 5,626,863 January 1995 Hubbell et al. Class 424/426 (University of Texas, Austin)
No. 0/60/118,093 February 1999 Hubbell et al. (Univ. Zurich/ETH) (pending)

What is claimed is:

1. A method of repairing a defect in an annulus fibrosus of an intervertebral disc, without excising the entire nucleus pulposus of the disc, comprising:
    filling at least a portion of a defect in said annulus fibrosus with an in situ curable, bio-compatible polymerizable or polymeric material composition;
    contacting at least a portion of said annulus fibrosus surrounding said defect with said curable composition; and
    curing said material in situ;
    thereby binding said cured material to at least a portion of said annulus fibrosus in an amount and over an area that is sufficient to at least impede exuding or extruding of nucleus pulposus material from said disc through said defect.

2. A method as claimed in claim 1 wherein said curable material is in flowable liquid form.

3. A method as claimed in claim 1 wherein said curable material comprises a combination of at least two components, and wherein at least one of said components is a cross linkable material and at least one other of said components is a cross linking agent for said cross linkable material.

4. A method as claimed in claim 3 wherein said cross linking agent is a polymeric compound having at least two epoxy groups therein.

5. A method as claimed in claim 3 wherein said cross linking agent is a chemical cross linking agent that is reactive with said cross linkable material.

6. A method as claimed in claim 1 wherein said defect is an opening in said annulus fibrosus that has been caused surgically.

7. A method as claimed in claim 1 wherein said defect is an opening in said annulus fibrosus that has been caused by herniation.

8. A method as claimed in claim 1 wherein said curable material comprises at least one polymeric component.

9. A method as claimed in claim 1 wherein said curable material is cured in situ by the action of heat thereon.

10. A method as claimed in claim 1 wherein said curable material is cured in situ by the action of electromagnetic radiation thereon.

11. A method as claimed in claim 1 wherein said cross linkable material comprises a flowable, semi-solid material.

12. A method as claimed in claim 1 wherein said in situ cured material comprises a visco-elastic bio-compatible material that has physical properties that are at least substantially similar to the physical properties of said annulus fibrosus.

13. A method as claimed in claim 1 wherein said in situ curable material comprises a biological material.

14. A method as claimed in claim 1 wherein said in situ cured material is biodegradable over a period of time that is substantially equal to the period of time during which additional annulus fibrosus material grows to an extent sufficient to fill said defect.

15. A method as claimed in claim 1 wherein said in situ curing is accomplished in up to about 40 minutes.

16. A method as claimed in claim 15 wherein said in situ curing is accomplished after at least about 2 minutes.

17. A method as claimed in claim 1 wherein said cured material comprises a hydrogel.

18. A method as claimed in claim 1 wherein said defect in said annulus fibrosus comprises at least one fissure in the annulus fibrosus.

19. A method as claimed in claim 18 wherein said at least one fissure has been caused by disc degeneration.

20. A method of repairing an intervertebral disc, having a damaged annulus fibrosus and a damaged nucleus pulposus, comprising:
    adding artificial nucleus pulposus material that has physical properties that are substantially similar to the physical properties of the remaining natural nucleus pulposus material in a quantity sufficient to produce a composite of nucleus pulposus material and said artificial "nucleus pulposus" material of a volume that is substantially the same as the volume of nucleus pulposus material that would have been in the intervertebral disc had the disc been in an undamaged condition;
    adding an in situ curable polymerizable or polymeric sealant material, that is not the same material as said artificial nucleus pulposus material, and that, in a cured state, is bio-compatible with said damaged annulus fibrosus, into the damaged area of said annulus fibrosus in a quantity and in an area sufficient to, in combination with remaining annulus fibrosus material, laterally substantially surrounds said nucleus pulposus composition;
    in situ curing said sealant material to an extent sufficient to repair damage to said annulus fibrosus and to an extent sufficient to prevent extrusion and exudation of a substantial portion of said composite nucleus pulposus through said damage; and
    maintaining said cured sealant in effective contact with said annulus fibrosus for a time sufficient to cause said composite nucleus pulposus and said to annulus fibrosus to form an effective intervertebral disc.

21. A method as claimed in claim 20 wherein said artificial nucleus pulposus material comprises a hydrogel material.

22. A method of repairing a disc disposed in an intervertebral volume, wherein said disc has a damaged annulus fibrosus and a reduced quantity of nucleus pulposus material as compared to the amount of natural nucleus pulposus material normally present in said intervertebral disc volume, comprising:
    adding artificial nucleus pulposus material to any remaining natural nucleus pulposus material in a quantity sufficient to produce a composite of nucleus pulposus materials of a volume that is substantially the same as the volume of nucleus pulposus material that would have been in said intervertebral disc volume if said annulus fibrosus was in an undamaged condition;
    adding an at least partially cured polymerizable or polymeric sealant material, that is different from said artificial nucleus pulposus material, and that is bio-compatible with said damaged annulus fibrosus, into the damaged area of said annulus fibrosis in a quantity and in an area sufficient to, together with remaining natural annulus fibrosus material laterally substantially surround said nucleus pulposus composition; and
    maintaining said cured sealant in effective contact with the remnants of said annulus fibrosus material for a time sufficient to cause said composite nucleus pulposus and said composite annulus fibrosus to form an effective intervertebral disc.

23. A method of repairing a disc disposed in an intervertebral volume, wherein said disc has a damaged annulus fibrosus and a reduced quantity of nucleus pulposus material as compared to the amount of natural nucleus pulposus material normally present in said intervertebral volume, comprising:
    adding artificial nucleus pulposus material to remaining natural nucleus pulposus material in a quantity sufficient to produce a composite of nucleus pulposus material of a volume that is substantially the same as the volume of the nucleus pulposus in said intervertebral volume in an undamaged condition;
    adding an at least partially cured polymerizable or polymeric sealant material, that is bio-compatible with said damaged annulus fibrosus, into the damaged area of said annulus fibrosus in a quantity and in an area sufficient to laterally substantially surround said nucleus pulposus composition; and
    maintaining said cured sealant in effective contact with said annulus fibrosus for a time sufficient to cause said composite nucleus pulposus and said annulus fibrosus to form an effective intervertebral disc.

24. A method of repairing a defect in an annulus fibrosus of an intervertebral disc, without removing substantially all of the nucleus pulposus in said disc, comprising:
    admixing a curable bio-compatible material with a curing agent therefore;
    substantially immediately after said admixing, initiating curing of said material;
    filling at least a portion of a defect in said annulus fibrosus with a composition comprising said curing material;
    contacting at least a portion of said annulus fibrosus surrounding said defect with said curing composition; and
    completing the curing of said material in situ;
    thereby binding said cured material to at least a portion of said annulus fibrosus in an amount and over an area that is sufficient to at least impede exuding or extruding of nucleus pulposus material from said disc through said defect.

25. A method of repairing a defect in an annulus fibrosus of an intervertebral disc, without removing all of the nucleus pulposus remaining in said disc, comprising:
    admixing a curable bio-compatible material with a curing agent therefore;
    substantially immediately after said admixing, initiating and completing curing of said material into a visco-elastic substantially solid material;

substantially immediately after said curing is completed, filling at least a portion of a defect in said annulus fibrosus with a composition comprising said cured material; and contacting at least a portion of said annulus fibrosus surrounding said defect with said cured composition; and thereby binding said cured material to at least a portion of said annulus fibrosus in an amount and over an area that is sufficient to at least impede exuding or extruding of nucleus pulposus material from said disc through said defect.

* * * * *